United States Patent
Qiu et al.

(10) Patent No.: US 11,491,674 B2
(45) Date of Patent: Nov. 8, 2022

(54) PROPELLER AND METHOD IN WHICH A PROPELLER IS SET INTO MOTION

(71) Applicant: Max-Planck-Gesellschaft Zur Förderung Der Wissenschaften E.V., Munich (DE)

(72) Inventors: Tian Qiu, Stuttgart (DE); Peer Fischer, Freiburg (DE)

(73) Assignee: Max-Planck-Gesellschaft Zur Förderung Der Wissenschaften E.V., Munich (DE)

( * ) Notice: Subject to any disclaimer, the term of this patent is extended or adjusted under 35 U.S.C. 154(b) by 287 days.

(21) Appl. No.: 16/604,291

(22) PCT Filed: Apr. 11, 2018

(86) PCT No.: PCT/EP2018/059331
§ 371 (c)(1),
(2) Date: Oct. 10, 2019

(87) PCT Pub. No.: WO2018/189263
PCT Pub. Date: Oct. 18, 2018

(65) Prior Publication Data
US 2020/0031010 A1   Jan. 30, 2020

(30) Foreign Application Priority Data
Apr. 12, 2017 (EP) .................... 17166356

(51) Int. Cl.
*B26D 5/08* (2006.01)
*B26D 1/00* (2006.01)
(Continued)

(52) U.S. Cl.
CPC .............. *B26D 5/086* (2013.01); *A61B 17/00* (2013.01); *A61B 17/320758* (2013.01);
(Continued)

(58) Field of Classification Search
CPC .... A61B 17/320725; A61B 17/320758; A61B 2017/00292; A61B 2017/320733; B27G 15/00; B27G 15/02
See application file for complete search history.

(56) References Cited

U.S. PATENT DOCUMENTS 5,163,910 A   11/1992   Schwartz et al.
6,503,224 B1   1/2003   Forman et al.
(Continued)

FOREIGN PATENT DOCUMENTS

| CN | 101109422 A | 1/2008 |
| CN | 103140303 A | 6/2013 |

(Continued)

OTHER PUBLICATIONS

Ghosh, Ambarish, et al "Controlled Propulsion of Artificial Magnetic Nanostructured Propellers", May 4, 2009 American Chemical Society, vol. 9, No. 6, pp. 2243-2245.
(Continued)

*Primary Examiner* — Tuan V Nguyen
(74) *Attorney, Agent, or Firm* — Harris Beach PLLC; Laura W. Smalley

(57) ABSTRACT

A method where a propeller is set into locomotion relative to a medium at least partially surrounding the propeller. An actuator induces a rotation of the propeller relative to the medium and about a rotational axis of the propeller, and the propeller converts its rotational movement into locomotion relative to the medium. The aspect ratio of at least one cross-section of the propeller is three or more. Also a helical or modifiedly helical propeller for converting rotational movement of the propeller into locomotion of the propeller relative to a medium at least partially surrounding the propeller, where the aspect ratio of at least one cross section of the propeller is three or more. And a method of producing a propeller, including the step of providing a plate extending
(Continued)

(a)

(b)

along the helical axis, where the aspect ratio of at least one cross section of the plate is three or more.

3 Claims, 11 Drawing Sheets

(51) Int. Cl.
    *A61B 17/00*     (2006.01)
    *A61B 17/3207*     (2006.01)
    *A61B 34/00*     (2016.01)
    *A61B 34/30*     (2016.01)

(52) U.S. Cl.
    CPC ............ *B26D 1/0006* (2013.01); *A61B 34/73* (2016.02); *A61B 2017/00345* (2013.01); *A61B 2017/320775* (2013.01); *A61B 2034/303* (2016.02); *B26D 2001/0073* (2013.01)

(56) References Cited

U.S. PATENT DOCUMENTS

| | | | |
|---|---|---|---|
| 8,768,501 | B2 | 7/2014 | Fischer et al. |
| 2007/0197959 | A1 | 8/2007 | Panotopoulos |
| 2009/0248055 | A1 | 10/2009 | Spivey et al. |
| 2012/0010598 | A1 | 1/2012 | Frassica et al. |
| 2014/0276840 | A1* | 9/2014 | Richter .............. A61B 17/1659 606/80 |
| 2015/0351856 | A1 | 12/2015 | Choi et al. |

FOREIGN PATENT DOCUMENTS

| | | |
|---|---|---|
| CN | 205268282 U | 6/2016 |
| EP | 2258440 A2 | 12/2010 |
| EP | 2674192 A1 | 12/2013 |
| JP | 2001179700 A | 7/2001 |
| JP | 2003325438 A | 11/2003 |
| JP | 2004016309 A | 1/2004 |
| JP | 2007504874 A | 3/2007 |
| JP | 2008508938 A | 3/2008 |
| JP | 2008279019 A | 11/2008 |
| JP | 2016511074 | 4/2016 |
| KR | 20130045001 A | 5/2013 |
| KR | 20150142149 A | 12/2015 |
| WO | WO-2008090549 A2 | 7/2008 |
| WO | WO-2011073725 A1 | 6/2011 |
| WO | WO-201625768 A1 | 2/2016 |

OTHER PUBLICATIONS

Ishiyama, K., et al "Swimming micro-machine driven by magnetic torque", 2001, Elsevier Science B.V., pp. 141-144.

Nelson, Bradley J., et al "Artificial bacterial flagella: Fabrication and magnetic control", Feb. 13, 2009, Applied Physics Letters, vol. 94 (3 pages).

Qiu, Tian et al "From Nanohelices to Magnetically Actuated Microdrills: A Universal Platform for Some of the Smallest Untethered Microbotic Systems for Low Reynolds Number and Biological Environments", 2013, Small Scale Robotics, pp. 53-65.

European Patent office, International Search Report, for corresponding International Application No. PCT/EP2018/059331, dated Jun. 7, 2018 (4 pages).

* cited by examiner

PROPELLER AND METHOD IN WHICH A PROPELLER IS SET INTO MOTION

CROSS-REFERENCE TO RELATED APPLICATIONS

This application is a national stage application under 35 U.S.C. § 371 of PCT Application No. PCT/EP2018/059331, filed Apr. 11, 2018, PROPELLER AND METHOD IN WHICH A PROPELLER IS SET INTO MOTION, published as WO 2018/189263 A1, which claims priority to and the benefit of European Patent Application No. 17166356.0, filed Apr. 12, 2017, which applications are incorporated herein by reference in their entirety.

FIELD OF THE INVENTION

The invention concerns a method in which a propeller is set into locomotion relative to a medium which at least partially surrounds the propeller, wherein an actuator induces a rotation of the propeller relative to the medium and about a rotational axis of the propeller, and wherein the propeller converts its rotational movement into locomotion of the propeller relative to the medium. It moreover concerns a helical or modifiedly helical propeller for converting rotational movement of the propeller into locomotion of the propeller relative to the medium. Furthermore, the invention concerns methods of producing the propeller.

BACKGROUND OF THE INVENTION

In many applications in medicine and biology it can be of advantage to be able to penetrate biological media, including biological fluids and soft tissues. For example, in minimally invasive procedures, such as the targeted delivery of substances or minimally invasive surgical procedures, it can be desirable to move a small untethered device to penetrate the medium, because such method potentially is less invasive and provides better control than methods that use larger or tethered devices.

Small untethered devices have been reported in the literature. For example, A Ghosh and P Fischer in "Controlled Propulsion of Artificial Magnetic Nanostructured Propellers," Nano Letters, vol 9, pp 2243 to 2245, 2009 and in the supporting information published with this paper demonstrate that the rotation of a cork-screw-like shape can produce forward propulsion in a fluid. The rotation is effected by a rotating magnetic field. This concept is also described in U.S. Pat. No. 8,768,501 B2. A swimmer with a slightly different shape is disclosed in the publication of L Zhang, J J Abbott, L X Dong, B E Kratochvil, D Bell, and B J Nelson, "Artificial bacterial flagella: Fabrication and magnetic control, "Applied Physics Letters, vol 94, p 064107, 2009. This swimmer, too, is driven by rotating magnetic field. K Ishiyama, M Sendoh, A Yamazaki, and K I Arai in "Swimming micro-machine driven by magnetic torque," Sensors and Actuators A: Physical, vol 91, pp 141 to 144, 2001 describe a screw, several millimetres in length, that penetrates a bovine tissue (meat) sample when brought into rotation by a rotating magnetic field.

T Qiu, J Gibbs, D Schamel, A Mark, U Choudhury, and P Fischer in "From Nanohelices to Magnetically Actuated Microdrills: A Universal Platform for Some of the Smallest Untethered Microrobotic Systems for Low Reynolds Number and Biological Environments," Small-Scale Robotics, From Nano-to-Millimeter-Sized Robotic Systems and Applications, vol 8336, I Paprotny and S Bergbreiter, 1st ed Berlin: Springer, pp 53 to 65, 2014 describe the manufacture of a cork-screw-like propeller by means of a glancing angle deposition method (GLAD) and of a propeller that more resembles a conventional screw by means of micro injection moulding. They also describe locomotion of the propellers in agarose gel when the propellers are actuated by means of a rotating magnetic field.

In all of the above disclosures, the propeller has a part with a permanent magnetic moment orthogonal to its long axis or the propeller is attached to a permanent magnet. Application of an external rotating magnetic field exerts a torque that spins the untethered propeller and causes its translation through a medium.

WO 2008/090549 A2 discloses a medical device for insertion into an organ of a patient that can be set into repetitive motion by an external magnetic field. WO 2016/025768 A1 discloses nanoparticles that can move along the gradient of a magnetic field originating from permanent magnets or electromagnets. The nanoparticles have a high tendency to attach to targeted cells, and an electric field can be applied to the nanoparticles to generate actions that are sufficient to cause death of the targeted cells. WO 2011/073725 A1 discloses a handheld automated biopsy device with a drill-like tip. The device can be brought into rotation by an actuator.

EP 2 674 192 A1 discloses a medical implantable device that can be implanted into a human or animal body. It comprises to intertwined helical wires, one of which will upon rotation be screwed into the tissue. US 2012/0010598 A1 discloses a catheterization system that is provided with an external thread and can be advanced into a bodily passageway by means of rotation. US 2009/0248055 A1 discloses a tissue penetrating surgical device. A distal tip of the device is at least partly covered by a fabric and the device can drill into the tissue by means of rotating the fabric.

It can be challenging to further miniaturise existing devices. Moreover, it has proven difficult to obtain propulsion in viscoelastic media with existing devices. The known cork-screw-like shapes work well in viscous liquids such as water and glycerol and in elastic solids such as agarose and meat. However, many important tissues in the biomedical domain are neither purely viscous fluids nor purely elastic solids. Rather, they are viscoelastic media that exhibit the combined properties of both a liquid and a solid. The inventors have found that the known propeller shapes can be inefficient in viscoelastic media.

Problem to be Solved by the Invention

It is an objective of the present invention to provide an improved method in which a propeller is set into locomotion relative to a medium which at least partially surrounds the propeller, wherein an actuator induces a rotation of the propeller relative to the medium and about a rotational axis of the propeller, and wherein the propeller converts its rotational movement into locomotion of the propeller relative to the medium. It is another objective of the present invention to provide an improved helical or modifiedly helical propeller for converting rotational movement of the propeller into locomotion of the propeller relative to the medium. Also it is an objective of the present invention to provide an improved propeller. It is a further objective of the invention to provide improved methods of producing the propeller. It is achievable with the present invention to address one or more of the afore-mentioned difficulties in the prior art.

Solution According to the Invention

In one aspect of the invention, the problem is solved by providing a method in which a propeller is set into locomotion relative to a medium which at least partially surrounds the propeller. An actuator induces a rotation of the propeller relative to the medium and about a rotational axis of the propeller, and the propeller converts its rotational movement into locomotion of the propeller relative to the medium. The aspect ratio of at least one cross section of the propeller—which cross section is a cross section related to the propeller's rotational axis—is 3 or more.

The inventors have found that such large aspect ratio can considerably increase propulsion, in particular in viscoelastic media. Without being bound to a particular theory, the inventors believe that the invention exploits a newly discovered propulsion mechanism that employs an elastic deformation of the medium by the propellers rotation. A large aspect ratio can induce a large deformation and thus strong propulsion.

In the context of the present invention, the term "propeller" refers to a propelling structure that can effect locomotion of itself or the load attached to itself relative to a medium. In the context of the present invention, the cross section's "aspect ratio" is the largest radius of the cross section divided by the smallest radius of the cross section, the radii extending from the cross section's centre to a point of the circumference of the cross-section. The cross section's centre is the point where the axis to which the cross section is "related" pierces the cross section. The cross section moreover is perpendicular to the axis to which it the cross section is "related". The circumference of the cross section is the outer boundary of the cross section. Accordingly, if the cross section is related to the propeller's rotational axis, the radii for determining the aspect ratio extend from the point where the rotational axis perpendicularly pierces the cross section to a point of the circumference of the cross section. Likewise, if the propeller is a helix (see below) and the cross section is related to the propeller's helical axis, the radii for determining the aspect ratio extend from the point where the helical axis perpendicularly pierces the cross section to a point of the circumference of the cross section.

In another aspect of the invention, the problem is again solved by providing a method in which a propeller is set into locomotion relative to a medium which at least partially surrounds the propeller. An actuator induces a rotation of the propeller relative to the medium and about a rotational axis of the propeller, and the propeller converts its rotational movement into locomotion of the propeller relative to the medium. In this aspect of the invention, the aspect ratio of at least one cross section of the rotating body that comprises the propeller and the parts of the medium that due to the rotation the propeller have been severed from the remainder of the medium and rotate with the propeller, which cross section is a cross section related to the rotating body's rotational axis, is 3 or more. Advantageously, with this aspect of the invention it is achievable that the parts of the medium that due to the rotation the propeller have been severed from the remainder of the medium rotate at the same speed as the propeller.

This embodiment of the invention is based on the inventors' discovery that parts of the medium can be severed—for example due to adherence—from the remainder of the medium and as a result rotate with the propeller. The inventors found that such co-rotation can considerably impede propulsion but that by means of a high aspect ratio of the rotating body comprising of the propeller(s) and the co-rotating part of the medium strong propulsion can nevertheless be achieved. Again without being bound to a particular theory, the inventors believe that in the newly discovered propulsion mechanism the propulsion predominantly results from the elastic deformation of the medium that does not co-rotate with the propeller and that as a result, the aspect ratio of the rotating body comprising of the propeller and the co-rotating part of the medium is critical for achieving strong propulsion.

In yet another aspect of the invention, the problem is solved by a helical or modifiedly helical propeller for converting rotational movement of the propeller into locomotion of the propeller relative to a medium which at least partially surrounds the propeller. The aspect ratio of at least one cross section of the propeller, which cross section is a cross section related to the propeller's helical axis, is 3 or more.

In the inventors' experiments, helical and modifiedly helical shapes have proven particularly suitable for achieving propulsion. Moreover, helical and modifiedly helical shapes have proven easy to manufacture.

In the context of the present invention, a propeller is "helical" (further below also referred to as a "helix") if its three-dimensional shape can be obtained by extending a two-dimensional shape along a curve while rotating the two-dimensional shape. The two-dimensional shape is extended along a curve (further below also referred to as "helical axis") such that any two cross sections of the propeller, if each cross section is taken perpendicularly to the curve at the point where the curve pierces the cross section, can be brought to coincide with the two-dimensional shape. The helical axis is the curve along which the two-dimensional shape is extended. A helix is chiral. In the context of the present invention, a propeller is "chiral" if its shape is distinguishable from its mirror image's shape; in other words, a propeller has chirality if its image in a plane mirror, ideally realized, cannot be brought to coincide with itself. The propeller can also be chiral by virtue of the orientation of its magnetic moment relative to the body of the propeller; such propellers are defined as "generalized chiral" in the context of the present invention. This includes objects that have an achiral body shape, but possesses a suitably oriented magnetic moment to render the propeller chiral.

In the context of the present invention, "modifiedly helical" (further below also referred to as a "modified helix") differs from helical in that the two-dimensional shape does not remain the same but changes as it is extended along the curve. The evolution of the two-dimensional shape is continuously differentiable (as opposed to discontinuous or non-differentiable, in a mathematical sense). For example, the two-dimensional shape may be stretched or compressed in one dimension, it may be bent, or it may be shrunken or enlarged proportionally in both dimensions. As a result of the latter for example a section of the propeller or even the entire propeller may have a tapered shape.

In a further aspect of the invention, the problem is solved by a method of producing a propeller, which method comprises the steps of (1) defining a straight helical axis; (2) providing a plate extending along the helical axis, the aspect ratio of at least one cross section (preferably all cross sections) of the plate, which cross section is a cross section related to the helical axis, is 3 or more; and (3) applying to the plate a torque along the helical axis, thereby twisting the plate into helical shape.

This method exploits the inventor's insight that the high ratio of width or length to thickness that is inherent in the definition of a plate can be translated into an aspect ratio of a helix if the helix is twisted by means of applying a torque. The inventors have discovered that this makes for an easy and reliable manufacturing method of a helical propeller with a high aspect ratio.

In yet a further aspect of the invention, the problem is solved by a method of producing a propeller, which method comprises the steps of (1) providing a first structure with a defined geometry; (2) moulding of the first structure in a second material, removing the first structure from the second material to generate a negative replicate of the first structure; (3) injecting a moulding material or moulding materials into the negative mould and curing the moulding material to form a second solid structure under given physical and chemical conditions; and (4) releasing the second solid structure from the negative mould, thereby obtaining the defined propeller.

The invention can advantageously be employed in medical diagnosis and therapy, including endoscopy, biopsy, delivery of drug or implant or radioactive matter, local heat generation. For example, the propeller may carry payloads attached to the propeller and release the drug at the disease location. In tumour therapy, the propeller can propel through the normal tissue to the tumour tissue, if the propeller is made of or comprises a metallic and magnetic material, heat can be generated in the material by inductive heating to kill tumour cells. Also, the propeller can drag a thin flexible tube to the tumour site, and drug can be continuously delivered to the tumour though the tube. Similarly, the propeller can drag an electrode connected with an electric wire and move to a particular region of the brain to measure the neuron electrical signal or apply an electric stimulation.

PREFERRED EMBODIMENTS OF THE INVENTION

Further preferred features of the invention which may be applied alone or in combination are discussed in the dependent claims, description below and the figures.

In a preferred embodiment of the invention, the aspect ratio of at least one cross section, preferably all cross sections, of the propeller, is/are 2 or more, more preferably 3 or more, more preferably 5 or more, more preferably 10 or more, more preferably 20 or more, more preferably 50 or more, more preferably 100 or more; the cross section(s) are related to the propeller's rotational axis or, alternatively, to the propeller's helical axis. This embodiment of the invention exploits the inventors' finding that a particularly high aspect ratio can entail a particularly strong propulsion. The cross section preferably is of a continuous shape.

Preferably, at least one cross section, more preferably every cross-section, of the propeller related to the propeller's rotational axis has a cross-sectional area that is at least 50%, more preferably 100%, more preferably 300%, more preferably 1 000% of the cross-sectional area—in the same cross sectional plane—of the parts of the medium that due to the rotation the propeller(s) have been severed from the remainder of the medium and rotate with the propeller(s). This embodiment exploits the inventors' find that co-rotating medium may impede propulsion and that by limiting the amount of co-rotating material such impediment can be limited.

Preferably, in case of at least one cross section, more preferably in case of all cross-sections, of the propeller the propeller's rotational axis passes through the area of the cross section, ie through the inside of the cross section's circumference; the cross section(s) are related to the propeller's rotational axis or, alternatively, to the propeller's helical axis. In other words, in a preferred embodiment of the invention, the rotational or the helical axis passes at least partly through the propeller.

Preferably, at least 20%, more preferably at least 50%, more preferably at least 80%, more preferably at least 95% of the surface area of the propellers has a surface roughness Ra (pursuant to Deutsches Institut für Normung DIN 4760) of less than 3.2 μm, more preferably less than 1.6 μm, more preferably less than 0.4 μm, more preferably less than 0.025 μm, more preferably less than 0.006 μm. With this embodiment of the invention it can advantageously be achieved that the adherence of medium, such as biological tissue, to the propeller, which adherence may impeding locomotion, is reduced. The surface roughness of the propeller is low to minimize the adhesion of the medium on the surface of the propeller.

Preferably, in order to minimize adhesion, the material from the propeller, at least at the surface of the propeller, is a metal, an anti-adhesion polymer and/or a biocompatible polymer. Coating can be applied to the surface of the propeller to minimize the adhesion of the medium onto the surface of the propeller. Special actuation methods that induce large shear on the surface, for instance, sudden start or stop of a large-angle rotation, large-angle oscillation, can be applied to minimize the attachment of the medium. For example, an oscillation of the propeller can be applied with a gradually increased amplitude from 10° to 300° and/or a gradually increased frequency from 0.1 Hz to 10 Hz, before the full rotation of the propeller. Due to the viscoelasticity of the medium, eg shear-thinning effect, the actuation method lowers the required starting torque for full rotation of the propeller.

In a particularly preferred embodiment of the invention, the low surface roughness is achieved by means of an at least partially coating of the surface of the propeller, More preferably the entire surface of the propeller is coated. Preferred coating materials include Teflon, PEG (Polyethylene glycol), Titanium or a combination thereof.

In a preferred embodiment of the invention, the aspect ratio of at least one cross section, preferably all cross sections, of the rotating body that comprise(s) the propeller and the parts of the medium that due to the rotation the propeller have been severed from the remainder of the medium and rotate with the propeller, which cross section(s) is/are a cross section related to the rotating body's rotational axis, is/are 2 or more, more preferably 3 or more, more preferably 5 or more, more preferably 10 or more, more preferably 20 or more, more preferably 50 or more, more preferably 100 or more. This embodiment of the invention exploits the inventors' finding that while co-rotation can impede propulsion, by means of a high aspect ratio of the rotating body comprising of the propeller(s) and the co-rotating part of the medium strong propulsion can nevertheless be achieved. The cross section of the rotating body preferably is of a continuous shape.

The preferred propeller is chiral. More preferably the propeller is helical or modifiedly helical. This embodiment of the invention is based on the inventors finding that chiral and in particular helical and modifiedly helical shapes can be particularly effective for achieving propulsion. Moreover, helical and modifiedly helical shapes have proven easy to manufacture. Preferably, the helical axis is a straight. If the propeller or the propeller is a helix or a modified helix, the rotational axis preferably coincides with the helical axis. The preferred helical or modifiedly helical propeller has a constant pitch.

A preferred propeller has a forward taper on at least one end, more preferably on two opposite ends. In the context of the present invention, a "forward taper" means that the propeller towards an end of the propeller is becoming gradually smaller or thinner. Preferably, the front end of the propeller is provided with a forward taper. In the context of the present application, the "front end" is the leading side of the propeller with regard to the direction of locomotion It is an achievable advantage of this embodiment of the invention that the taper can decrease the area of contact with the medium at the front end of the propeller. It can be achieved that—in particular if the medium has viscoelastic properties—the pressure which the propeller applies on the medium is larger than the tensile strength of the medium.

In one embodiment, the tip of the taper is located on the rotational axis of the propeller, and/or on the helical axis, provided that the propeller is a helix. In another embodiment, the tip is located eccentrically, ie away from the rotational axis, and/or away from the helical axis, provided that the propeller is a helix. Particularly preferably the tip is located near the outer perimeter, with respect to the rotational axis or helical axis of the propeller. This embodiment can exploit the fact that many media have shear-thinning properties so that a large shear rate can help the forward propulsion of the propeller. As the velocity is the greatest at the outer perimeter of the propeller, a tip located there can achieve the greatest shear rate.

The largest radius of any cross section of the propeller that is perpendicular to the propeller's rotational axis or helical axis preferably is 5 mm or less, more preferably 3 mm or less, more preferably 1 mm or less, more preferably 500 µm or less, more preferably 300 µm or less, more preferably 100 µm, or less, more preferably 50 µm or less, more preferably 30 µm or less.

The smallest radius of any cross section of the propeller that is perpendicular to the propeller's rotational axis or helical axis preferably is 300 µm or less, more preferably 100 µm or less, more preferably 50 µm or less, more preferably 30 µm or less, more preferably 10 µm or less, more preferably 5 µm or less, more preferably 3 µm or less.

The length of the propeller divided by the largest radius of any cross section of the propeller that is perpendicular to the propeller's rotational axis or helical axis preferably is 0.5 or more, more preferably 1 or more, more preferably 3 or more, more preferably 5 or more.

Preferably, the propeller is untethered. In the context of the present invention, "untethered" means that the propeller has no material connection—for example in the form of a wire, a tube or a rod—to the space outside the medium by which the propeller is at least partly, preferably completely, surrounded. Alternatively the propeller is minimally-tethered, whereas the driving torque for the propeller is applied wirelessly, but the propeller is connected to a passive element, for example to pull the end of a tube and/or a wire, which other end is outside the medium, into a particular position inside the medium. The tether can be used for material transportation, signal measurement or stimulation, but the tether is passive that it does not provides active driving force or torque to the propeller. Alternatively the propeller is tethered, for example the driving torque of the propeller is input by a string, a wire or a rod, whose rotation leads to the locomotion of the propeller together with the tether.

The rotation of the propeller preferably is induced remotely. In the context of the present invention "effected remotely" means that means that induce the rotation of the propeller are located at a distance from the propeller that is at least 5 times the largest diameter of the propeller in any dimension. In a preferred embodiment of the invention, the rotation of the propeller is induced remotely by means of a magnetic field. Thus, the source of the magnetic field is located at a distance from the propeller that is at least 5 times the largest diameter of the propeller in any dimension, and the source of the magnetic field acts as an actuator for inducing the propeller's rotation. Preferably, the source of the magnetic field is outside the medium which at least partly, preferably completely, surrounds the propeller.

The magnetic field preferably is rotated, thereby inducing a rotation in the propeller. As the magnetic moment of the propeller tends to align with the external magnetic field and the propeller rotates along the axis that exhibits minimal resistance, the orientation of the propeller is determined by the rotating external magnetic field. The magnetic field can be applied foe example by a set of electric coils, e.g. Helmholtz coils, or permanent magnets.

Preferably, if the magnetic field exerts a magnetic gradient force on the propeller in the direction of locomotion, this force is so weak that alone it cannot effect locomotion of the propeller. More preferably, the magnetic field has no gradient component in the direction of locomotion. The preferred magnetic field is stronger than 1 G (gauss), more preferably stronger than 10 G, more preferably stronger than 50 G. The preferred magnetic field is weaker than 10 000 G, more preferably weaker than 1 000 G, more preferably weaker than 500 G, for example 100 G.

Preferably, for inducing the rotation by means of a magnetic field, the propeller is at least partly magnetized or a component materially connected with the propeller is at least partly magnetized. The magnetization is preferably permanent. For this purpose, the propeller comprises a magnetised or magnetisable material; for example, it consists of the magnetised or magnetisable material, or it contains magnetised or magnetisable material, or it is coated with the magnetised or magnetisable material. Suitable materials include Fe, Co, Ni, or magnetic alloy, preferably comprising some or all the afore-mentioned metals. The preferred magnetisable material of the propeller is magnetized in the direction of the maximal length on its cross-section.

In addition or alternatively, an actuator is provided that, like the propeller, is at least partly, preferably completely, surrounded by the medium and materially connected with the propeller. For example, the actuator may be an electrical or a molecular motor; the material connection may comprise a drive shaft. An energy reservoir—such as an electrical battery—for this actuator may likewise be at least partly, preferably completely, surrounded by the medium; preferably, in this case a material connection—for example a wire or a tube—is provided between the reservoir and the actuator to provide the actuator with the energy source, for example electricity or a chemical stored in the energy reservoir. In addition or alternatively the actuator preferably is provided with an energy receiver to receive energy in an untethered fashion from an energy transmitter located the space outside the medium, ie there is no material connection between the energy transmitter and the energy receiver.

Preferably, the torque applied to the propeller when inducing the rotation of the propeller(s) is smaller than 100 mN·mm (millinewton millimetres), preferably smaller than 50 mN·mm, 10 mN·mm, 5 mN·mm, 1 mN·mm.

Preferably the propeller is operated at a speed below 0.9 times its step-out frequency, more preferably below 0.8 times, more preferably below 0.7 times, more preferably below 0.5 times the propellers step-out frequency. Preferably the propeller is operated at a speed above 0.05 times its step-out frequency, more preferably above 0.1 times, more preferably above 0.2 times, more preferably above 0.3 times the propellers step-out frequency. In the context of the present invention, the "step-out-frequency" is the frequency at which the torque is not strong enough to overcome the medium's drag forces. The step-out frequency can for example be measured by driving the propeller with a rotating magnetic field; If the magnetic field rotates sufficiently slowly, the propeller synchronously rotates with the field. There exists a field rotation frequency, however, above which the applied magnetic torque is not strong enough to keep the propeller synchronized with the filed. This is the step-out-frequency.

In a preferred method according to the invention the propeller is completely surrounded by the medium. With this embodiment of the invention particularly strong propulsion can be achieved as all parts of the propeller are in permanent contact with the medium.

The preferred medium is viscoelastic. In the context of the present invention "viscoelastic" refers to media which exhibit both viscous and elastic characteristics when undergoing deformation. A particularly preferred medium is a viscoelastic fluid, where the viscous property is dominant over the elastic property at the applied shear frequency (or shear stress), for example synovial fluid, vitreous humour, mucus. Another particularly preferred medium is a viscoelastic solid, where the elastic property is dominant over the viscous property at the applied shear frequency (or shear stress), for example connective tissue, brain tissue, Matrigel®.

The preferred medium is a biological tissue. A particularly preferred biological tissue is tissue of the brain, the kidney, the prostate, the urinary bladder, a blood vessel, the liver, the pancreas, the breast, the lung, the skin, fat tissues, connective tissues, vitreous humour, mucus, or tumour tissue.

Preferably, the rotation of the propeller induces a strain in the medium, whereby the strain causes a change in the medium's elastic energy, which in turn causes the translation of said propeller.

In a preferred embodiment of the invention a load is attached to the propeller for being moved relative to the medium by the propeller. The preferred load may comprise molecules, nanoparticles, porous polymer matrix, porous silicon and/or one or more electric circuits that are attached to the propeller. Advantageously, the electronic circuit(s) may control the motion of the propeller. Alternatively or in addition one or more tubes and/or wires which are pulled from outside to inside of the medium may be attached to the propeller.

The trajectory of the locomotion preferably is controlled remotely, for example by changing the direction and/or rotational frequency of the magnetic field or by changing the direction, rotational axis, direction of rotation and/or rotational frequency of the actuator at least partly surrounded by the medium. Also, multiple propellers according to the invention may be combined into one device, and in such case individually changing the rotational frequency of the propellers can be used control the propulsion direction of the device. Preferably a controller, for example an appropriately equipped and programmed PC is connected with the actuator (eg the source of the magnetic field or the actuator at least partly surrounded by the medium) to control the trajectory of the locomotion.

The trajectory of the locomotion preferably is imaged and/or measured, for example by one or more or the following imaging methods: light microscopy, fluorescence imaging, x-ray imaging, computer tomography (CT), magnetic resonance imaging (MRI), positron emission tomography (PET), infrared imaging, ultrasound imaging.

The propeller may for example be made of or comprise one or more metal, for example copper, gold, cobalt, nickel, iron, steel, titanium, and or one or more polymer, for example Teflon, PLA, PMMA, PC, and or one or more semiconductor, for example silicon, or a combination of such materials. In a particularly preferred embodiment of the invention, the propeller can be made of biodegradable material. It is achievable advantage of this embodiment of the invention that after deployment into the tissue, no retrieval is needed as it can be degrade and absorb by the body. The propeller may for example consist of two or more sections, one rigid section for propulsion and one biocompatible section for drug carrying and release.

Suitable methods of manufacturing the propeller include moulding, in particular injection moulding, electrodeposition, direct writing, 3D printing and machining. A preferred manufacturing method comprises the steps of (1) defining a straight helical axis; (2) providing a plate extending along the helical axis, the aspect ratio of at least one cross section—preferably all cross sections—of the plate, which cross section(s) is/are related to the helical axis, is/are 2 or more; and (3) applying to the plate a torque along the helical axis, thereby twisting the plate into helical shape. In a next step, the helix can be cut into one or multiple individual propeller(s) of the desired length. It is an achievable advantage of this method that the propeller can be manufactured easy and reliably.

Another particularly preferred manufacturing method comprises the steps of (1) providing a first structure with a defined geometry; (2) moulding of the first structure in a second material, removing the first structure from the second material to generate a negative replicate of the first structure; (3) injecting a moulding material into the negative mould and curing the moulding material to form a second solid structure under given physical and chemical conditions; and (4) releasing the second solid structure from the negative mould, thereby obtaining the defined propeller, wherein the moulding material is a mixture of at least two component materials. Preferred component materials include polymer materials, magnetic materials, drug molecules, radioactive materials. Thus the moulding material may for example consist of a polymer material and a magnetic material.

The curing conditions preferably include at least one of the following: temperature, pH, magnetic field, electric field, acoustic field, light field and radiation. For example, the mixture is epoxy resin mixed with ferromagnetic particles, and the polymer is cured at room temperature within a magnetic field in the direction perpendicular to the helical axis;

Drugs can be incorporated in mixture in the step (3) above, or be absorbed to the propeller materials after releasing in the step (4) above. With this method, the structure, magnetization and functionalization of the propeller can be achieved in a single process.

BRIEF DESCRIPTION OF THE FIGURES

The invention is illustrated in greater detail with the aid of schematic drawings.

DETAILED DESCRIPTION OF THE INVENTION

Propeller Moving in a Tissue Model

Figure 2:
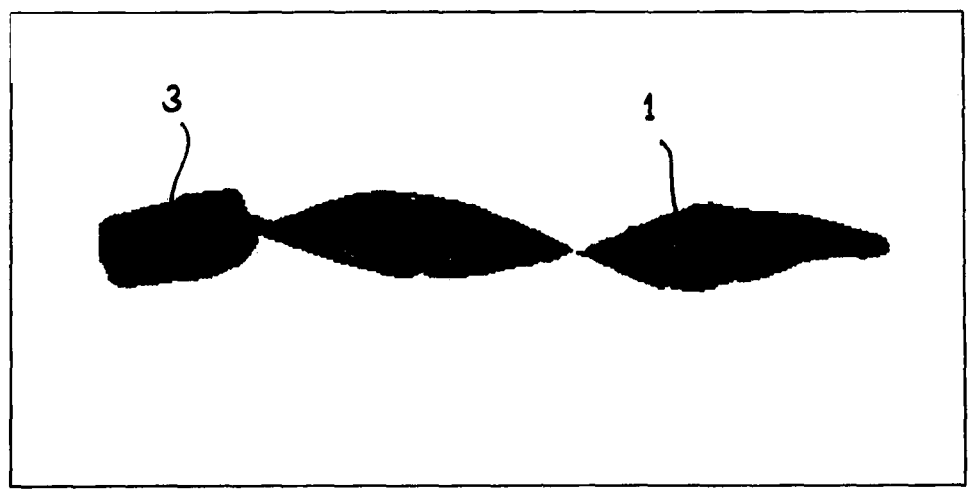
FIG. 2 is a light microscope image of a propeller according to the invention to which a magnet is attached and which is embedded in soft tissue.

It is an achievable advantage of the propeller 1 according to the invention that it can efficiently self-propel through a viscoelastic medium, for example a biological tissue. In FIG. 2, a propeller 1 according to the invention is shown that is fully embedded in a gel medium 2 of Matrigel®, a hydrogel that is used as a tissue model for the validation of the propeller. Matrigel®, available from Gibco®, Life Technologies® is the trade name for a gelatinous protein mixture secreted by mouse sarcoma cells. It resembles the complex extracellular matrix (ECM) found in many tissues, and it is widely accepted as an in vitro model for cell 3D culture, tumour cell metastasis studies and cancer drug screening. Here, Matrigel® serves as a gel medium 2 model for connective tissues for the propeller 1 to penetrate. The Matrigel® solution was used as received, thawed on ice and gelled in an incubator under 37° C. for 1 hour.

The propeller 1 was inserted into the gel medium 2 by means of tweezers. A magnetic field with a homogeneous magnitude (adjustable from 50 to 1000 Gauss) and a continuous rotating direction (frequency in the range of 1 to 100 Hz (hertz) was applied, and the field was rotated with a speed of 10 Hz. One end of the propeller 1 a cylindrical magnet 3 of a neodymium, iron and boron (NdFeB) material, 200 μm (micrometres) in diameter and 400 μm in length and magnetized in the diameter direction is attached in a torque-proof fashion. The magnet has a permanent magnetic moment and rotates together with the external rotating magnetic field. Due to the special shape design of the propeller, it couples the rotation to translational motion (forward or backward propulsion) and achieves net displacement in the gel medium 2 or biological tissues.

Figure 1:
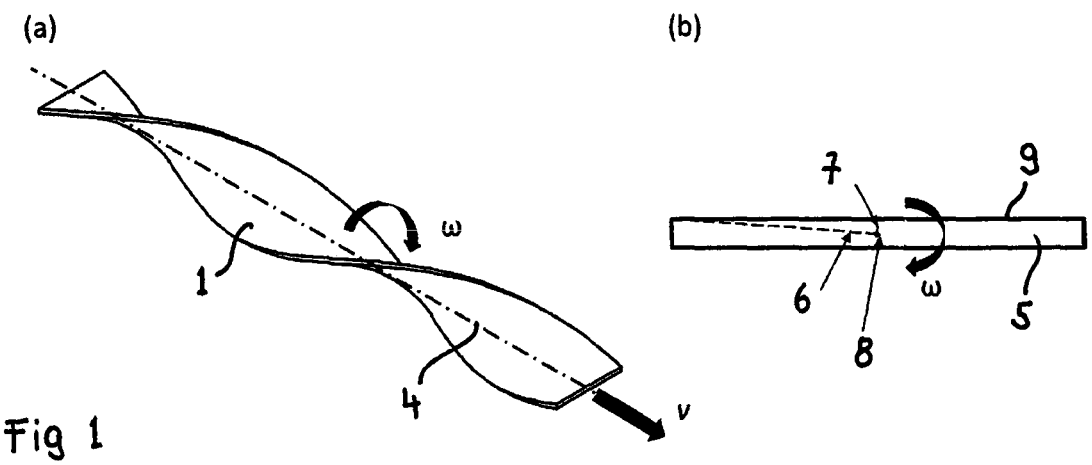
FIG. 1(a) is a perspective view of an embodiment of the propeller according to the invention in perspective view.
FIG. 1(b) is a cross sectional view of the propeller of FIG. 1(a)

As can be best seen in FIG. 1(a), the propeller 1 has a chiral, more precisely a helical shape. It is left-handed but of course a right-handed design would be suitable likewise. The axis of rotation 4 and the helical axis coincide in the propeller of FIG. 1. The direction of locomotion v is indicated as a rightwards arrow v. The direction of rotation is indicated as a semi-circular arrow ω. As can be seen in the cross-sectional view in FIG. 1(b), the aspect ratio of any cross-section 5 of the propeller 1 perpendicularly to the helical axis is considerably larger than 5. The aspect ratio is obtained by dividing the largest radius 6 of the cross section by the smallest radius 7 of the cross section 5. The radii 6, 7 extend from the point 8 where the rotational axis 4 perpendicularly pierces the cross section 5 to a point of the circumference 9 of the cross section.

Figure 3:
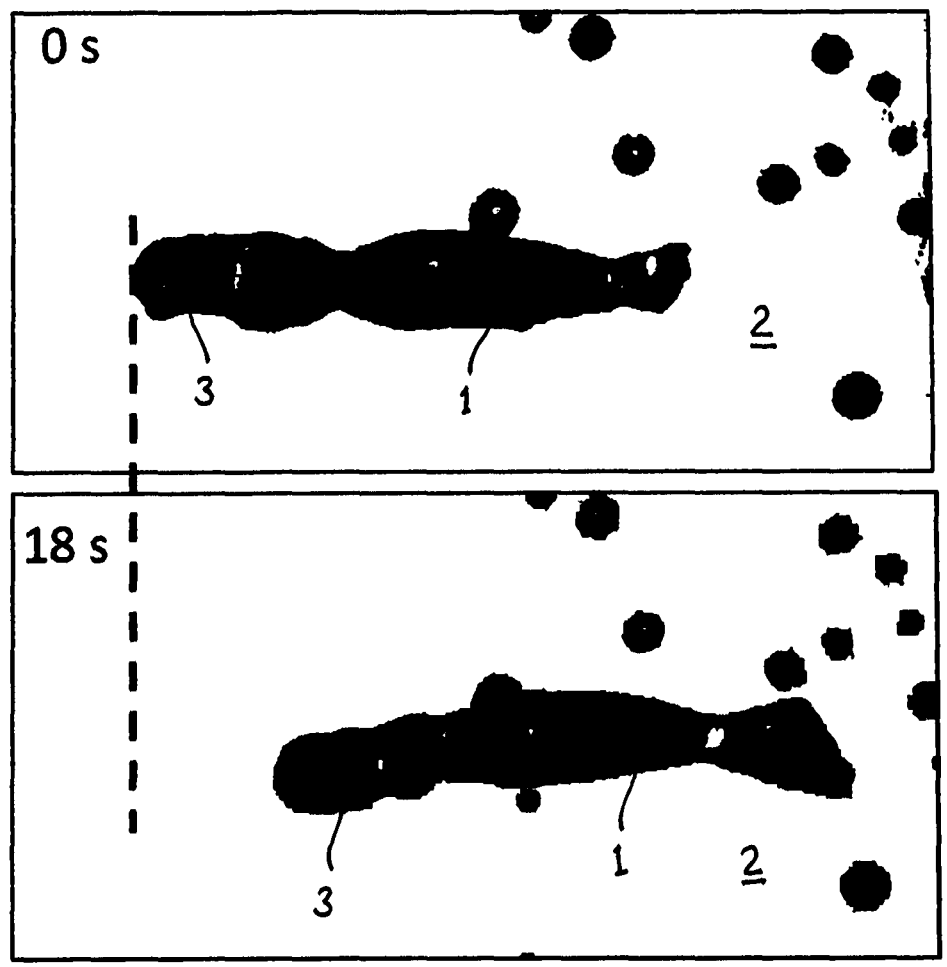
FIG. 3 shows two light microscope images of the propeller of FIG. 2 penetrating a Matrigel®, the bottom image taken 18 seconds after the top image.

From the images in FIG. 3 it can be seen how the propeller 1 propagates through the Matrigel® gel medium 2. The bottom image was taken 18 seconds after the top image. The dotted line indicates the initial position of the magnet 3. A speed of approximately 45 μm/s (micrometres per second) along the helical axis of the propeller was observed at the rotational frequency of 10 Hz. By choosing the rotational direction of clockwise or counter-clockwise, the propeller 1 can move either forward or backward.

Figure 4:
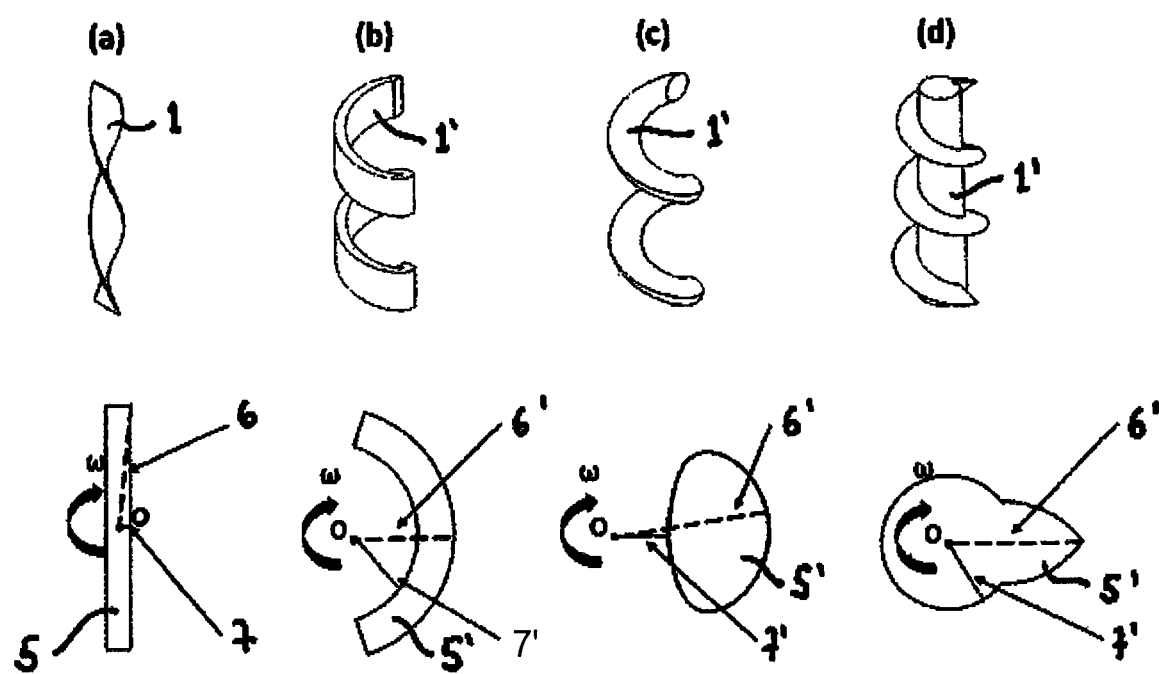
FIGS. 4(a) to (d) schematically compare the cross-sectional shapes of a propeller according to the invention as shown in FIG. 4(a) with those of prior art propellers as shown in FIGS. 4(b) to 4(d)

In FIGS. 4(a) to (d) schematically the cross-sectional shape of a propeller 1 according to the invention is compared with cross-sectional shapes of propellers known from the afore-mentioned publications by L Zhang, J J Abbott, L X Dong, B E Kratochvil, D Bell, and B J Nelson, FIG. 4(b), A Ghosh and P Fischer, FIG. 4(c) and T Qiu, J Gibbs, D Schamel, A Mark, U Choudhury, and P Fischer, FIG. 4(d). In the top row, 3D views are provided while in the bottom row the cross-sectional shapes are shown. It can be seen that the cross section 5 of the propeller of the present invention has a considerably larger aspect ratio than the cross sections 5' of the prior art propellers 1' based on their radii 6' and 7'.

Figure 5:
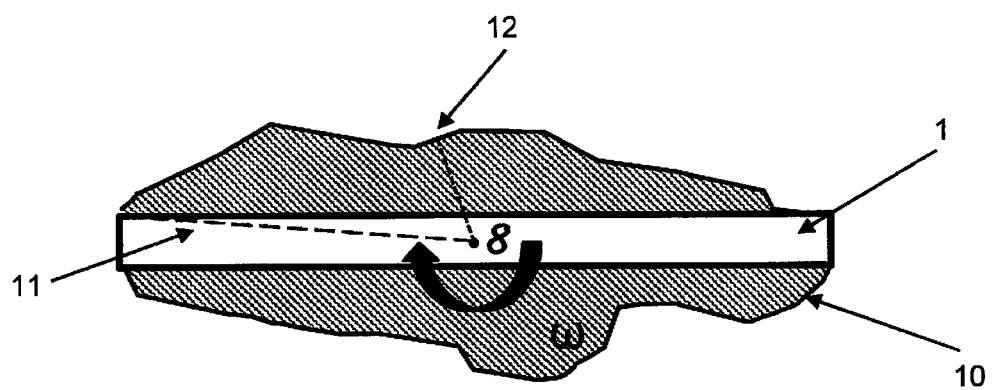
FIG. 5 is a schematic cross-sectional representation of a propeller according to the invention with medium co-rotating with the propeller.

Moreover, as the propeller 1 rotates in and moves through the viscoelastic medium 2, parts 10 the medium 2 may attach to the surface of the propeller 1 and rotate together with it. This is schematically shown in FIG. 5. In the example of FIG. 5 the aspect ratio of the cross section of the rotating body that comprises the propeller 1 and the parts 10 of the medium 2 that rotate with the propeller 1 is still larger than 3. The aspect ratio in this case is obtained by dividing the largest radius 11 of the cross section of the rotating body by the smallest radius 12 of the cross section of the rotating body. The radii 11, 12 extend from the point 8 where the rotational axis 4 perpendicularly pierces the cross section to a point of the circumference 9 of the cross section of the rotating body.

Propulsion Mechanism of the Propeller

Figure 6:
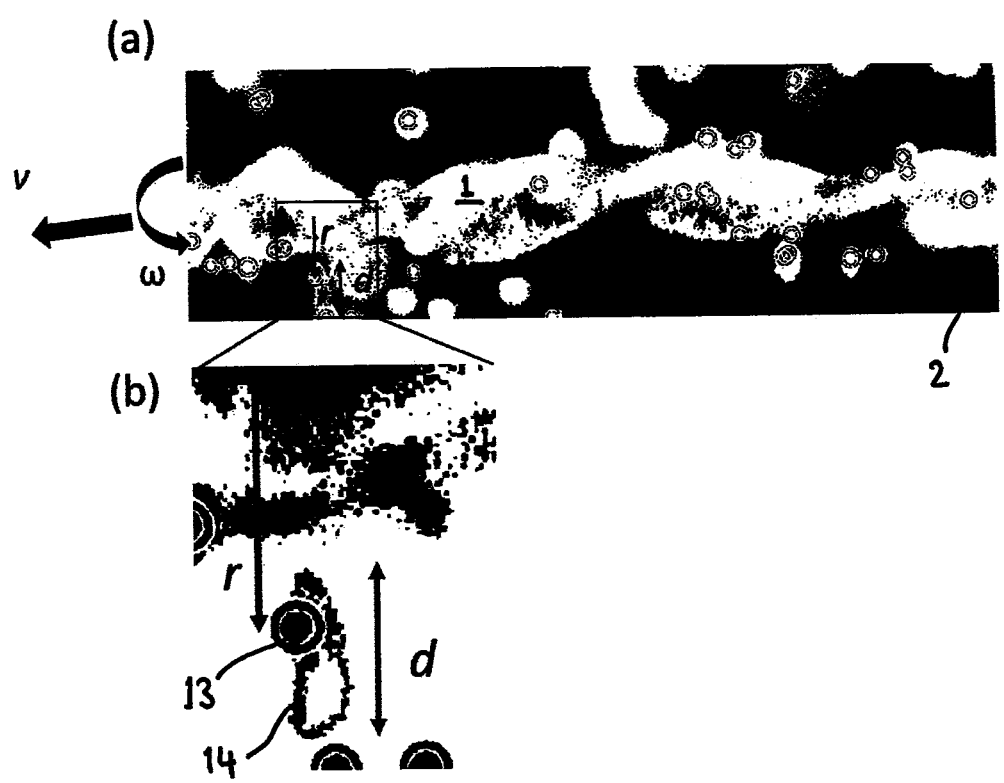
FIG. 6(a) shows a frame from a video of the propeller in a viscoelastic medium with tracer particles embedded in the medium to visualize the deformation of the medium.
FIG. 6(b) indicates the trajectory of one tracer particle over the period of many rotations of the propeller; the large normalized deformation provides large axial propulsion force.

The inventor believe, without prejudice, that the propeller 1 according to the invention when used in viscoelastic media exploits a new propulsion mechanism, which is different from the mechanism for propulsion in viscous fluids as has been published before. FIGS. 6(a) and 6(b) show results of a Particle Imaging Velocimetry (PIV) experiment. In the experiment, fluorescent polystyrene beads (FluoSpheres®, Life Technologies), 15 µm in diameter, were used as tracer particles and mixed in the Matrigel® gel medium 2 to show the movement, in particular the deformation, of the gel medium 2. The beam of a green laser with a wavelength of 532 nm (nanometres) was expanded by a cylindrical lens to a laser sheet and directed on a thin sheet of the Matrigel® gel medium 2. The motion of the propeller 1 and the tracer particles was recorded by a microscope with a long pass filter (OD4-550 nm, Edmund Optics) and a video camera. The position of the tracer particles were analysed by a customized script in Matlab (R2014b, Mathworks), and circled in every frame of the video. The circles can be seen in both FIG. 6(a) and the enlarged FIG. 6(b). In FIG. 6(b) the trajectory of one tracer particle 13 is indicated. The particle 13 follows a closed, essentially elliptical trajectory 14 over a period of many rotations of the propeller 1. A normalised deformation can be calculated as the quotient of radial displacement d and the distance r from the rotational axis.

The experiment suggests that the movement (deformation) of the viscoelastic medium 2 is clearly different from the flow around a propeller in a viscous fluid. In a fluid, the particles rotate together with the propeller for a full rotation, and the difference of fluidic dynamic drag in the two perpendicular directions at low Reynolds number results in a forward propulsion force, which was explained in the literature. However, a different motion trajectory of the particles was observed with the propeller 1 disclosed here, suggesting that the new design of the propeller 1 enables a new propulsion mechanism in the viscoelastic media, which has not been reported before.

Figure 7:
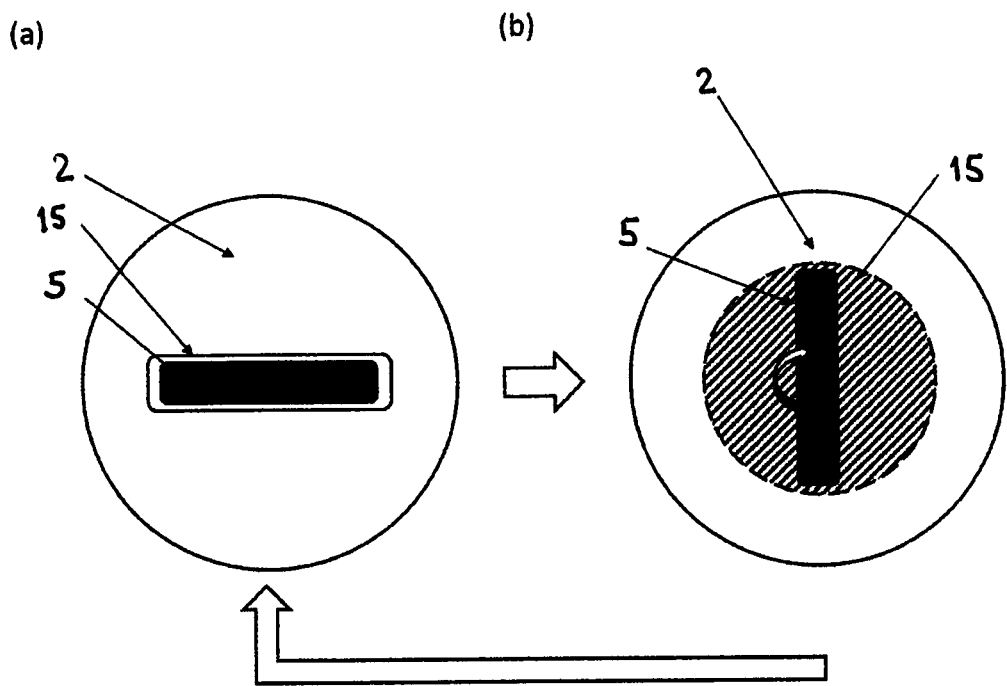
FIG. 7 illustrates in a cross-sectional view a propeller according to the invention rotating in a viscoelastic medium and the effectively deformed area of the medium induced by the rotation of the propeller is labelled with hatch.
Figure 8:
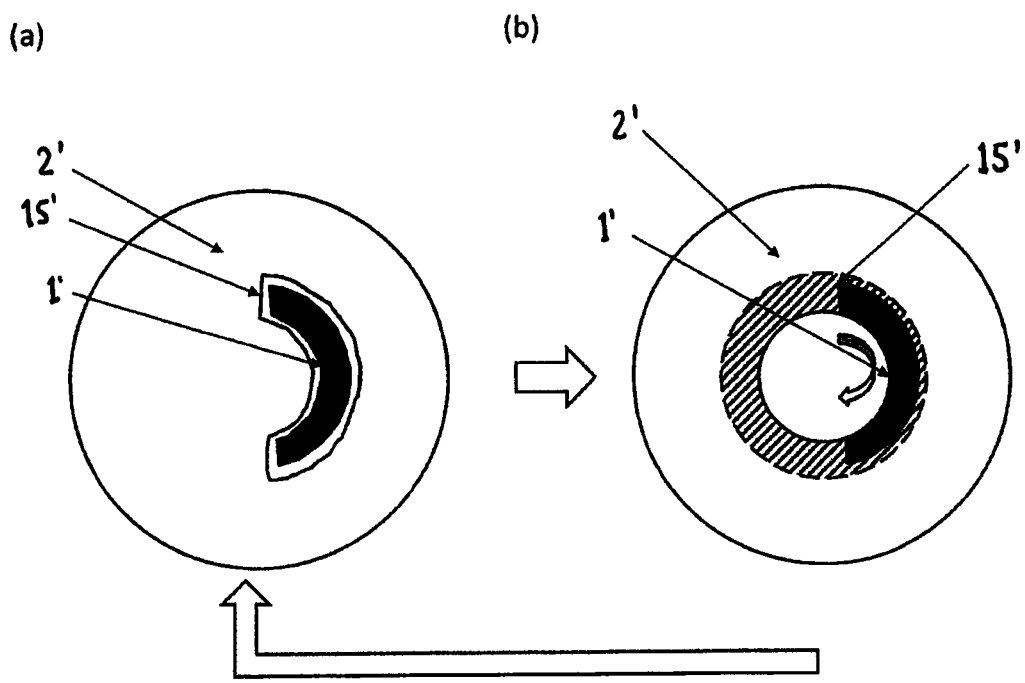
FIG. 8 illustrates in a cross-sectional view a prior art propeller design rotating in a viscoelastic medium and the effectively deformed area of the medium induced by the rotation of the propeller is labelled with hatch.
Figure 9:
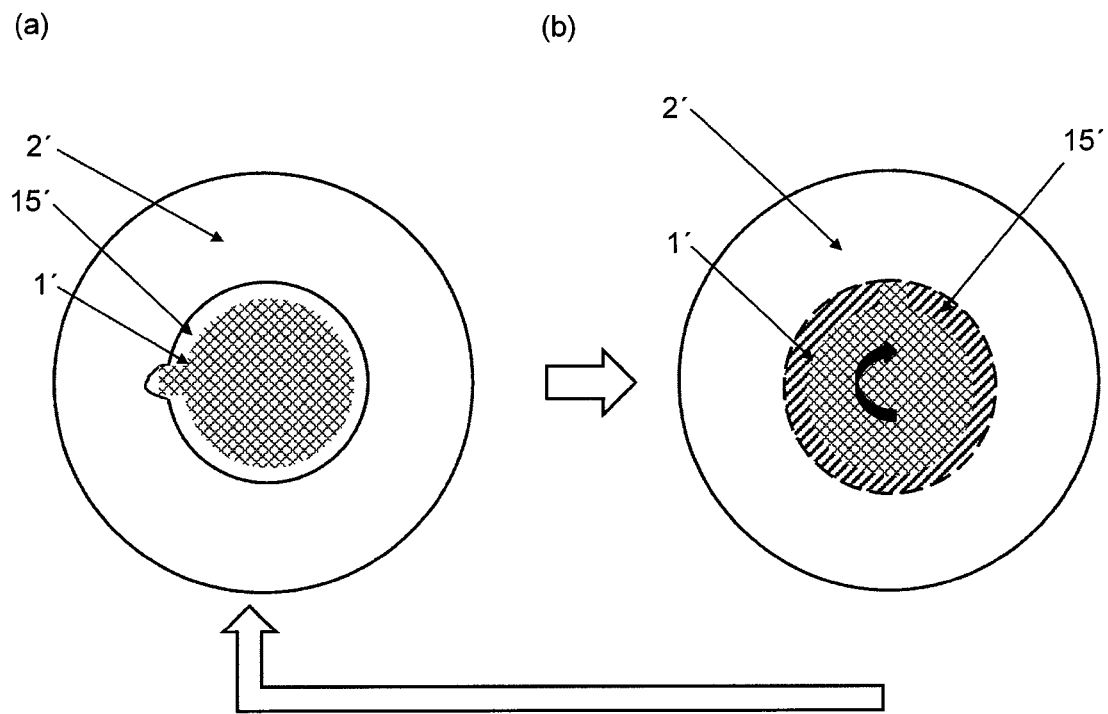
FIG. 9 illustrates in a cross-sectional view another prior art propeller design rotating in a viscoelastic medium and the effectively deformed area of the medium induced by the rotation of the propeller is labelled with hatch.

The relaxation time of the viscoelastic solids, which include most biological tissues, are often on the order of minutes, whereas the propeller typically rotates at a frequency of 1 to 10 Hz. As, accordingly, the cycle time (0.1 to 1 s) of the propeller's 1 rotation is much shorter than the relaxation time, only the elastic response of the gel needs to be considered. As an example, shown in the FIG. 7, the cross-section 5 of the propeller 1 is modelled as a rectangular solid that rotates in an initially rectangular hole 15 of the medium 2. Note that in FIG. 7(b) the medium 2 is not flowing but is deformed as the propeller 1 rotates. Large deformation (strain) of the medium 2 is induced by the rotation of the propeller 1. The effectively deformed volume of the medium 2 around the propeller 1 is dramatically larger than in prior art propeller designs (as shown exemplarily in FIG. 8 where the corresponding elements are a propeller 1' in the form of a screw reported in prior art; and FIG. 9 where the corresponding elements are a propeller 1' in the form of a conventional screw. The medium 2', the gap 15' and the effective deformed area in hatch are also shown in the figures). The medium 2 is considered elastic, ie a spring where the recoil force is positively correlated to the deformation. Therefore, larger deformation of the medium 2 requires more torque for rotation, and exerts larger forward propulsion force. Both of these two phenomena were observed in the experiment.

Figure 10:
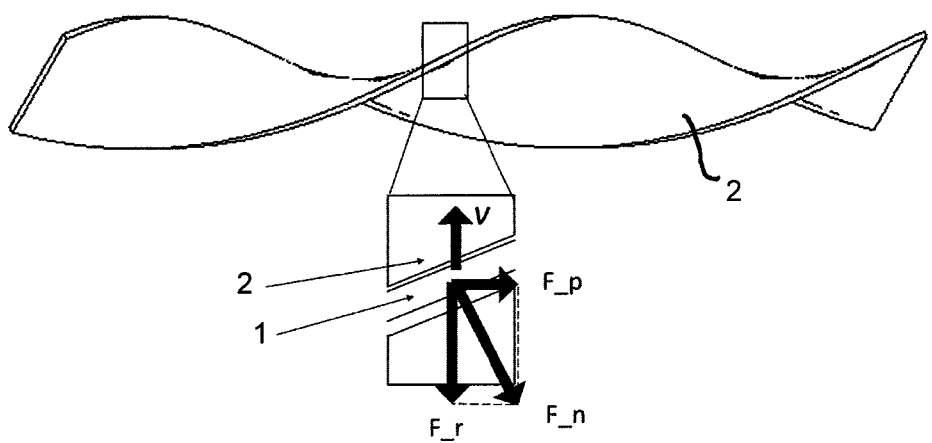
FIG. 10 is a force diagram of a short part on the edge of a propeller according to the invention.

For further illustration, in FIG. 10 the force diagram of a small section of the propeller 1 (left-handed, the front edge of the propeller rotates upwards in order to move to the right) is shown. The direction of rotation is indicated as an upwards arrow v. It is clear from the force diagram that there is a propelling force component F_p pointing towards the right. Similarly to the situation shown in FIG. 7, the larger the deformation, the larger is the forward propulsion force. Therefore, the proposed propulsion mechanism of the propeller 1 according to the present invention can be summarized in the following three aspects: First, the rotation of the propeller 1 induces large deformation of the gel medium 2. More specifically, large aspect ratio on the cross section 5 of the propeller 1 induces large deformation of the gel medium 2, which leads to large forward propulsion force F_p. Second, the pressure on the tip 16 of the propeller 1 should be higher than the tensile strength of the gel medium 2 in order to break it. It requires an area of the tip 16 as small as possible, for example, a sharp tip 16 is preferable. Moreover, the newly cut area (crack) 15 of the medium 2 due to the forward motion of the tip 16 of the propeller also has a high aspect ratio, such as a rectangular shape, shown as the white area in FIG. 7(a), which again allows the large deformation of the medium 12 when the propeller 1 rotates. It is different from the traditional propeller's 1' design that the crack 15' is almost circular, see FIG. 9(a), and the deformation of the medium 2' induced by the traditional propeller 1' is small. Third, after the possible attachment of the medium 2 around the propeller 1 such as FIG. 5, it should still fulfil the two conditions above. This criterion ensures a continuous movement of the propeller 1 in the tissue.

The traditional propeller 1' designs with a hollow opening in the middle, such as the published designs shown in FIG. 4(b) and FIG. 4(c), do not propel efficiently in viscoelastic media. The reason lies in that the opening is filled with the viscoelastic medium during rotation of the propeller, and when considering the medium rotating together with the propeller, the overall structure does not have a high aspect ratio on any cross-section, as shown in FIG. 8(b). In other words, a plug of the gel changes the traditional propeller shape into an almost cylindrical shape, inducing very limited deformation of the media around it, thus the traditional propellers can only rotate at the same position in the viscoelastic medium and no net displacement can be achieved. The present invention in a preferred embodiment clearly differs from the prior art designs in that on at least one cross section, preferably all the cross sections, which are perpendicular to the helical axis of the propeller, the axis passes through the propeller. Or in other words, on at least one cross-section, preferably all the cross-sections, the rotational centre is inside of the propeller.

For some particular kinds of viscoelastic media, such as a yield-stress fluid, the propeller can break (or liquefy) part of the medium due to the shear stress induced by the rotation of the propeller. And the transportation of the broken (or liquefied) parts of the medium to the backwards can also result in the forward propulsion of the propeller.

Preferably, the rotational speed that leads to highest propulsion speed should be used to actuate the propeller 1. This value, which depends on both the geometry of the propeller 1 and the rheology of the medium, can be determined experimentally by sweeping the frequency and measuring the propulsion speed. It has been found that the optimal frequency in a viscoelastic medium 2 of the propeller 1 disclosed here can be much lower than the step-out frequency. When the frequency is increased above the optimal value, the propeller 1 continues to rotate, but the propulsion speed dramatically decreases until it reaches zero. On the contrary, in viscous fluids at low Reynolds number, the optimal frequency of a propeller 1 is very close to the step-out frequency, and the propulsion speed increases linearly with the driving frequency before it reaches step-out. This observation too, suggests that the present propeller 1 enables a new propulsion mechanism in viscoelastic media.

Propeller Moving in a Brain Sample

Figure 11:
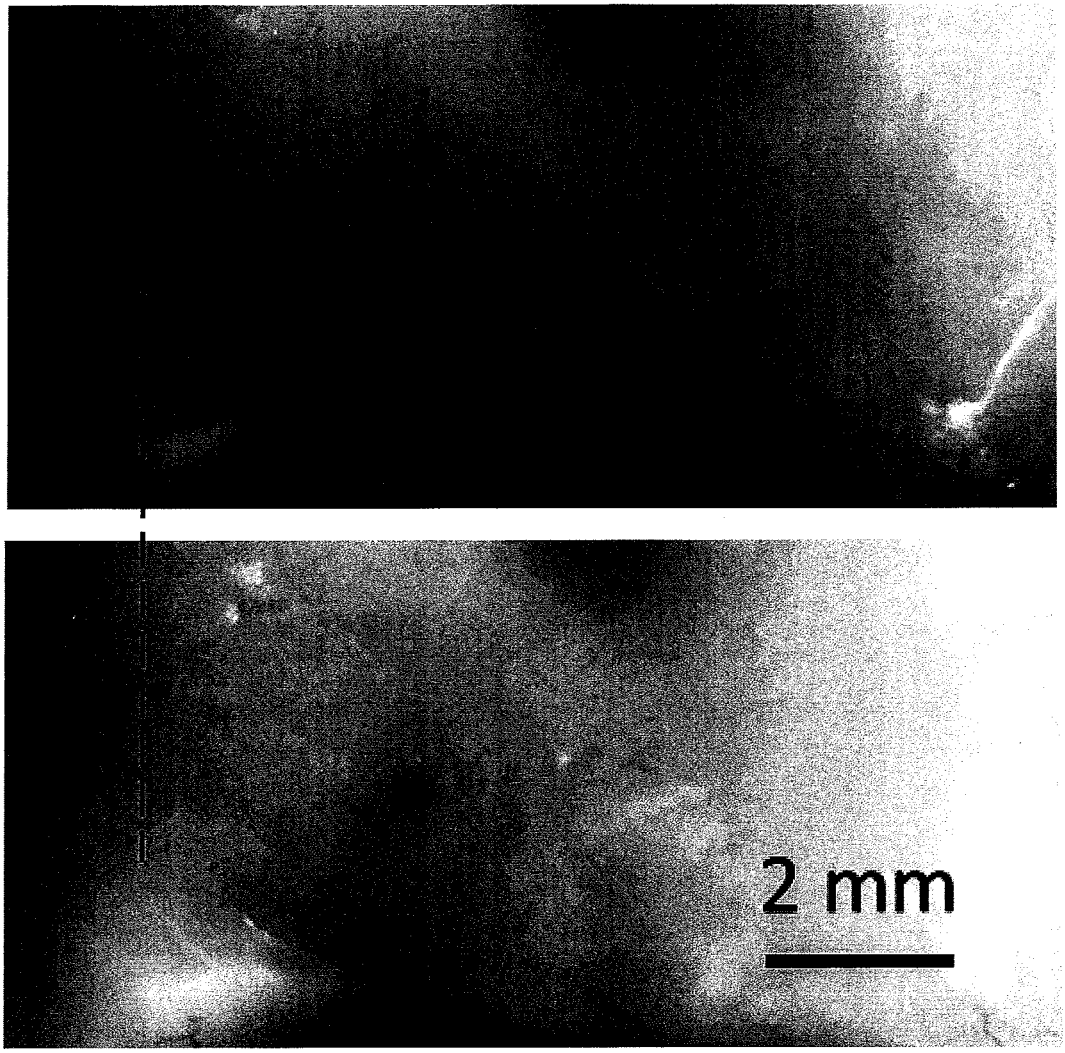
FIG. 11 shows two light microscope images of the propeller of FIG. 2 penetrating porcine brain tissue, the bottom image taken 300 seconds after the top image.

The light microscope photos in FIG. 11 show a propeller 1 according to the invention that penetrates a porcine brain tissue to demonstrate its capability to move through real biological soft tissues. Fresh porcine brain was stored on ice and received from a local slaughterhouse. A volume of about 25×25×8 mm$^3$ (cubic millimetres) of the brain was dissected, and the propeller 1 was inserted by tweezers. As the tissue was relatively thin, and bright white light back illumination was used, the movement of the propeller was observed inside the brain tissue. The dotted line indicates the initial position of the propeller 1. An average propulsion speed of approximately 35 µm/s was measured at a rotational frequency of about 1 Hz. Due to the shape of the propeller 1, the rotation of propeller 1 can be actuated with limited magnetic torque. In the experiment, a magnetic field with a magnitude of 100 to 300 G was sufficient to drive the propeller 1 through the brain tissue sample. This field is applicable with common magnetic field generators, such as electric coils or permanent magnets setup as discussed in more detail further below.

Fabrication of the Propeller

Figure 12:
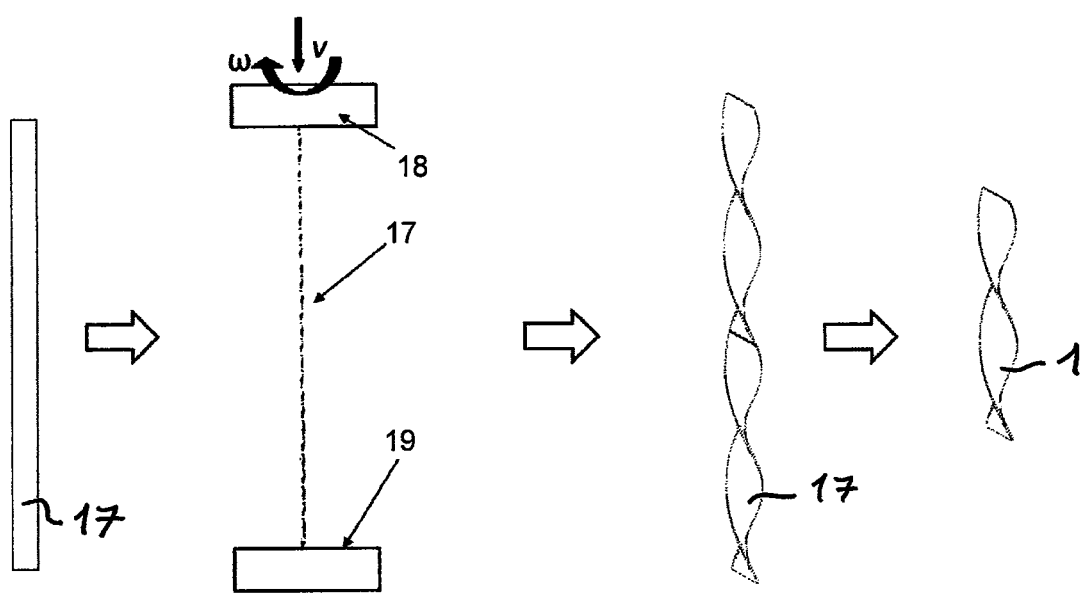
FIG. 12 illustrates the method of producing a propeller according to the invention.

A method of producing the propeller 1 according to the invention is illustrated in FIG. 12. The propeller 1 was made of copper with a mechanical machining approach. A copper wire, 50 µm in diameter, was mechanically rolled into a flat plate 17 with a width of 255 µm and a thickness of 13 µm. As shown in FIG. 12, the plate 17 was mounted between two concentric clamps 18, 19 which can be rotated relative to each other. By rotating one 18 of the clamps while leaving the other 19 stationary, the plate 17 was twisted into a chiral structure. During twisting, a normal force occurs on the axial direction v, thus the distance between the two clamps 18, 19 was adjusted accordingly. Sensors can be used to measure the force and torque during this process, and the distance and angular position of the clamp can be controlled by motors with a computer. The pitch dimension and chirality of the propeller can be controlled in this way. The long twisted plate 17 was subsequently cut into individual propellers 1 with a desired length of 2 mm. Finally, a miniaturized magnet, 200 µm in diameter and 400 µm in length, was attached to one tip of the propeller 1.

The cutting procedure can be done by machining, laser etching, (focused) ion etching, or chemical etching. The mask for etching can be fabricated by photolithography on the two sides of the plate before the twisting process. In this way, a mass production process of the propeller can be achieved.

Figure 13:
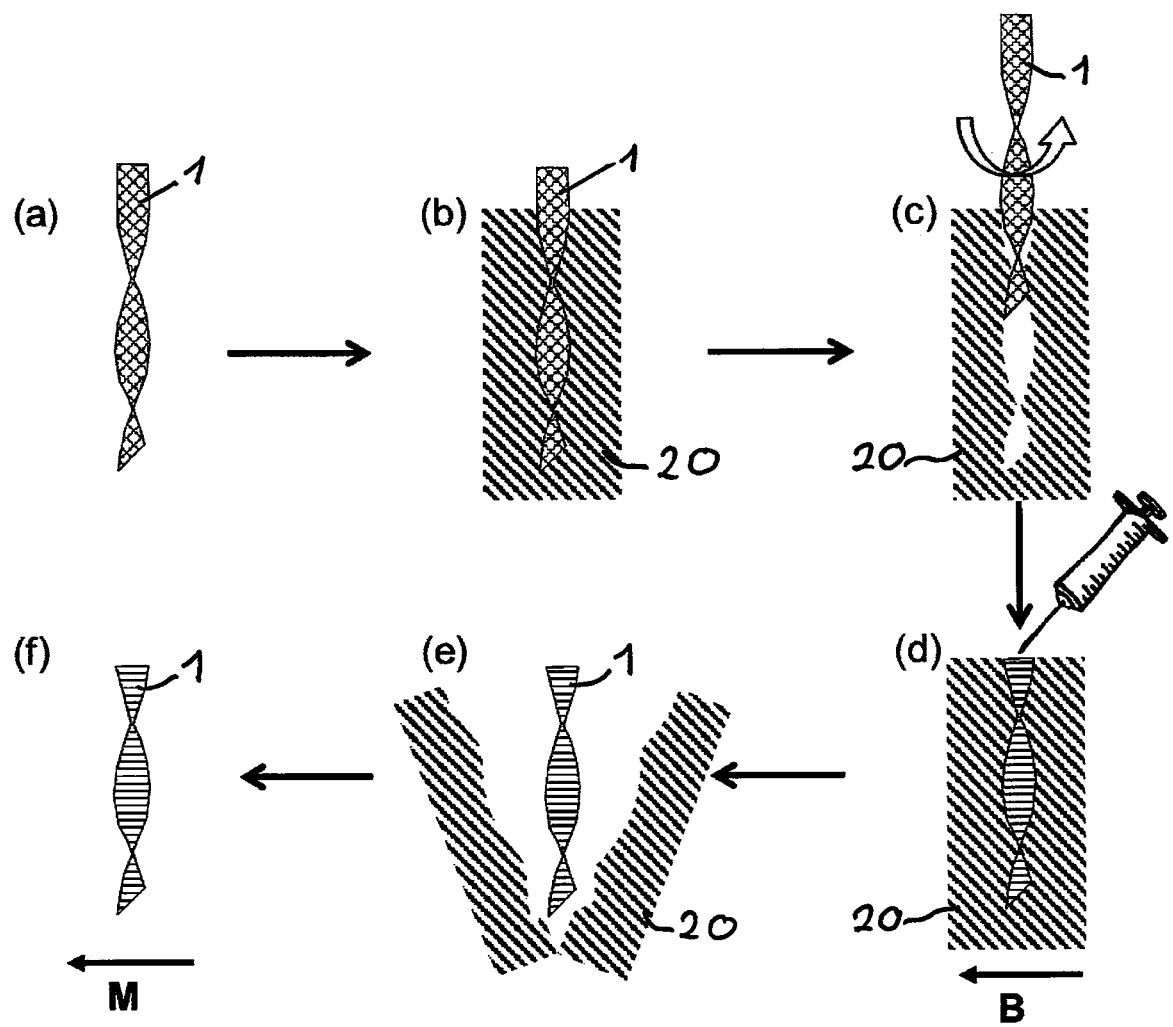
FIG. 13 illustrates another method of producing a propeller according to the invention.

Another method of producing the propeller 1 according to the invention is illustrated in FIG. 13. A structure of the propeller 1 is first obtained, for example in copper material by the method described above or by 3D printing (FIG. 13(a)); then, the structure is moulded into a second material, such as a soft polymer, eg PDMS (FIG. 13(b)); the first structure is removed from the negative mould 20, for example by rotating the propeller 1 in the right direction and it propels out of the mould 20, or by expanding the soft polymer mould 20 (FIG. 13(c)); liquid polymer material or mixture is injected into the negative mould 20 (FIG. 13(d)), for example a mixture of epoxy resin and ferromagnetic particles (mean diameter 40 µm), the polymer is cured at room temperature in the presence of an external magnetic field as illustrated by the arrow in the FIG. 13(d); finally, the propeller 1 is obtained by releasing it from the negative mould 20, either by breaking the mould 20, or by rotating the propeller 1 in the right direction and it propels out of the mould 20 (FIG. 13(e)). The propeller 1 have the right magnetic moment M (as indicated by arrow in (FIG. 13(f)), as the magnetic particles in the structure are aligned in the right direction when the external magnetic field B is applied. Drugs can be incorporated in polymer mixture in the moulding step above, or be absorbed to the propeller materials after releasing in the last step above.

Figure 14:
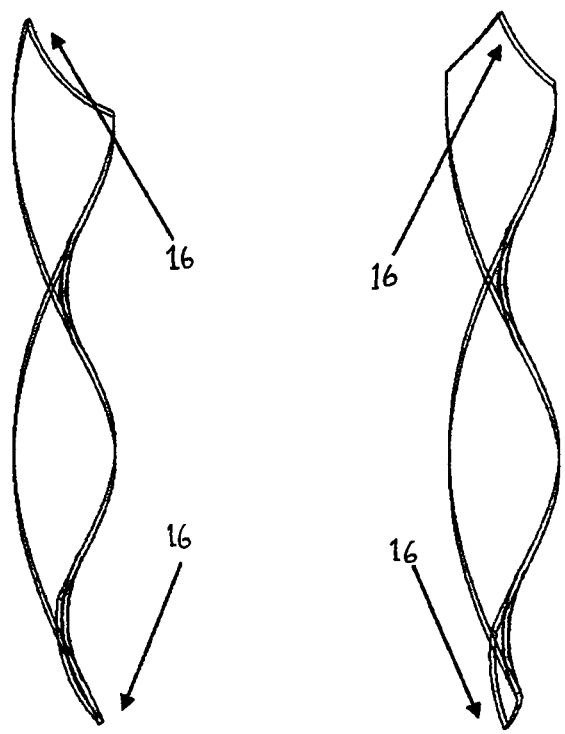
FIG. 14 is a perspective view of two propellers according to the invention with forward tapers at both ends.

FIG. 14 illustrates how the two tips 16 of the propeller 1 can be cut or etched or moulded into designed shape, preferably a sharp tip. This way, the pressure at the tip 16 can be increased by decreasing the contact area; also, the shear rate in the medium 2 in front of the propeller can be increased. As many biological media are shear-thinning, a larger shear rate also helps the forward propulsion of the propeller. In this case, the sharp tip of the propeller is preferably at the edge of the propeller tip 16 and far from the rotational axis.

Actuation of the Propeller

A suitable setup for inducing rotation into the propeller by means of a rotating magnetic field is for example known from the afore-mentioned publication by T Qiu, J Gibbs, D Schamel, A Mark, U Choudhury, and P Fischer. The relevant parts of this document are incorporated into the present disclosure by reference.

The field can be spatially homogeneous or with a magnetic gradient in space, but preferably the pulling force acting on the propeller generated by the magnetic gradient is in the same direction as the direction of the self-propelling force of the propeller 1. The magnetic field can be generated with electric coils. For example, three pairs of Helmholtz coil can achieve the motion control of the propeller in three dimensional space by changing the phase and magnitude of the current in different coils. The magnetic field can also be generated with the rotation of permanent magnet(s), which can be several magnets specially arranged in space or only one magnet keeping a required distance away from the propeller. To control the propulsion trajectory with the permanent magnets setup, the rotational axis of the setup should be changed.

For the realisation of the invention in its various embodiments, the features disclosed in the present description, claims and drawings can be of relevance individually as well as in any combination.

The invention claimed is:

1. A helical or modifiedly helical propeller for converting rotational movement of the propeller into locomotion of the propeller relative to a medium which at least partially surrounds the propeller, wherein the aspect ratio of at least one cross section of the propeller, which cross section is a cross section related to the propeller's helical axis, is 3 or more, and on at least one cross section which is perpendicular to the helical axis of the propeller, the axis passes through the propeller, and wherein the propeller is at least partly magnetized or further comprises a component materially connected with the propeller, which component is magnetized.

2. The propeller of claim 1, wherein the largest radius of any cross section of the propeller that is perpendicular to the propeller's rotational axis is 5 mm or less.

3. The propeller of claim 1, wherein the smallest radius of any cross section of the propeller that is perpendicular to the propeller's rotational axis is 300 µm or less.

\* \* \* \* \*